(12) United States Patent
Nahum et al.

(10) Patent No.: US 8,509,503 B2
(45) Date of Patent: Aug. 13, 2013

(54) MULTI-APPLICATION ROBOTIZED PLATFORM FOR NEUROSURGERY AND RESETTING METHOD

(75) Inventors: Bertin Nahum, Baillargues (FR); Lucien Blondel, Montpellier (FR)

(73) Assignee: Medtech S.A., Montpellier (FR)

( * ) Notice: Subject to any disclaimer, the term of this patent is extended or adjusted under 35 U.S.C. 154(b) by 908 days.

(21) Appl. No.: 12/452,142

(22) PCT Filed: Jun. 19, 2008

(86) PCT No.: PCT/FR2008/000860
§ 371 (c)(1),
(2), (4) Date: Dec. 17, 2009

(87) PCT Pub. No.: WO2009/013406
PCT Pub. Date: Jan. 29, 2009

(65) Prior Publication Data
US 2010/0137880 A1    Jun. 3, 2010

(30) Foreign Application Priority Data
Jun. 19, 2007  (FR) ..................... 07 04350

(51) Int. Cl.
*G06K 9/00*  (2006.01)
(52) U.S. Cl.
USPC ....................................................... 382/128
(58) Field of Classification Search
USPC ..... 382/128–134; 128/920–925; 356/39–49; 600/407–414, 424–426; 345/581–618
See application file for complete search history.

(56) References Cited

U.S. PATENT DOCUMENTS

| | | | |
|---|---|---|---|
| 2004/0024311 A1* | 2/2004 | Quaid, III | 600/428 |
| 2007/0121202 A1* | 5/2007 | Riederer | 359/377 |
| 2007/0270687 A1* | 11/2007 | Gardi et al. | 600/425 |
| 2009/0036918 A1* | 2/2009 | Burgess | 606/201 |
| 2009/0177081 A1* | 7/2009 | Joskowicz et al. | 600/426 |

\* cited by examiner

*Primary Examiner* — Atiba O Fitzpatrick
(74) *Attorney, Agent, or Firm* — Nath, Goldberg & Meyer; Jerald L. Meyer

(57) ABSTRACT

The invention relates to a multi-application robotized platform for neurosurgery, comprising: a planning console comprising processing means that can especially receive and process digital images; a positioning robot arm comprising a plurality of arm segments, one of which is terminal and proximal and the other is terminal and distal, said segments being interconnected by articulated elements, the terminal distal arm segment comprising a receiving element arranged in such a way as to receive tools, and the robot arm being guided by the planning console; at least one video image recording means able to record images of the anatomical region to be processed, said means being electrically connectable to the processing means of the planning console, and able to be positioned and fixed to the receiving element of the distal arm segment in a removable manner; tools, instruments and others suitable for being positioned and fixed to the receiving element of the terminal distal arm segment in a removable manner; means for observing pre-operating and per-operating images, said means being electrically connected to the planning console for receiving video signals therefrom relating to the images to be displayed, and/or to the image recording means. The invention also relates to a method ensuring an improved resetting of the anatomical region to be processed in relation to its digital model using said platform.

7 Claims, 6 Drawing Sheets

MULTI-APPLICATION ROBOTIZED PLATFORM FOR NEUROSURGERY AND RESETTING METHOD

This is a National Phase Application filed under 35 U.S.C. 371 as a national stage of PCT/FR2008/000860, filed on Jun. 19, 2008, an application claiming the benefit of French Patent Application 0704350, filed on Jun. 19, 2007, the content of each of which is hereby incorporated by reference in its entirety.

TECHNICAL FIELD

This invention is related to the field of materials used in medicine and more specifically in neurosurgery. It relates in particular to a multi-application robotized platform for neurosurgery and the associated implementation method.

STATE OF THE PRIOR ART

It is known that the practicing of neurosurgery requires the use of an ever increasing number of dedicated surgical materials and equipment.

Thus, stereotaxic frames are used in particular for tumoral biopsies or the accurate positioning of stimulation electrodes. A disadvantage of these frames is that they do not lend themselves well, or at all, to open surgery. Besides their size, another disadvantage resides essentially in that they require a firm anchorage in the bones of the cranium.

Also known are robots that can be used instead of stereotaxic frames.

Also known, from the state of the art, are neuro-navigation systems offering a solution applicable to open surgery. These systems permit the detection of anatomical structures based on a pre-operating imaging given by a scanner, by a magnetic resonance imaging (MRI) apparatus or the like, and on a three-dimensional localization system, comprising for example several light sources attached to the instrument, emitting in the infrared range.

These systems comprise in addition one or more cameras capable of perceiving the infrared and of emitting a signal that will be processed by an appropriate computer capable of calculating the data regarding the positions and orientations in space of the surgical instrument such as the position of the tip of the latter.

Typically, before the carrying out of the imaging, the skull of the patient is equipped with radio-opaque markers, in the form of pastilles, designed to be affixed next to the skin. The obtained digital images are transferred to a memory bank of the computer. With the help of the surgical instrument or of a specific instrument the surgeon brings the tip of this instrument in contact with each of the radio-opaque markers. Thus, the position of the instrument can be located with respect to the previously obtained digitized medical images. In this way, during the surgical action in particular, the image of the instrument and its position can be superimposed to the digital images in view of displaying them jointly on a display screen.

The neuro-navigation systems are in particular used for the detection and resection of cerebral tumors.

Also known are surgical microscopes used as visualization tools during open neurosurgical actions (ex.: corticectomy).

The surgical applications described above and the equipment associated thereto represent a considerable portion of the routine practice in neurosurgery.

However, the plurality of the pieces of equipment and their specificity pertaining to a type of neurosurgical application are disadvantageous in the hospital logistical management, and conflicting with the objectives of flexibility and versatility of the operating theater.

Another disadvantage specific to neuro-navigation resides in the possibilities of errors of resetting between the established digital model, the patient, and the tool. This is related essentially to the fact that radio-opaque pastilles are affixed on the skin, which remains a moving element, and not implanted fixedly in the cranial bones.

For the positioning of these radio-opaque markers, the practitioner tries however to avoid any invasive procedure despite the risk of loss of resetting precision due to the involuntary displacement of one of the markers.

Also known from the state of the art is a robotized guiding device for surgical tools. Such a tool is in particular described in patent application FR 2 871 363. This robotized device includes a robot arm, means for collecting anatomical marks with the help of the robot arm, means for processing these anatomical marks and means for automatic positioning of an instrument for guiding a surgical tool, this guiding instrument being carried by the robot arm.

This guiding device is not provided with means for recording images of the field of operation or with specific means for visualization of the field of operation.

This device does not meet the objective pursued by this invention.

EXPOSITION OF THE INVENTION

This invention aims at solving the problems mentioned above by providing, on the one hand, a multi-application solution substituting all devices listed above and, on the other hand, a method aiming at an improved resetting of the digital model of the anatomical region to be processed with the patient and the surgical tool.

To this end, the multi-application robotized platform for neurosurgery is essentially characterized in that it comprises:
  a planning console comprising processing means capable, in particular, of receiving and processing digital images,
  a positioning robot arm comprising a plurality of arm segments, one of which is terminal and proximal and the other is terminal and distal, said segments being interconnected by articulated elements and the terminal distal arm segment comprising a receiving element arranged in such a way as to receive tools, instruments, and the like, said robot arm being guided by the planning console,
  at least one video image recording means capable of recording images of the anatomical region to be processed, said recording means being electrically connectable to the processing means of the planning console, and said recording means being capable of being positioned and removably fixed to the receiving element of the terminal distal arm segment,
  tools, instruments, and the like designed to be positioned and removably fixed to the receiving element of the terminal distal arm segment,
  means for displaying pre-operating and per-operating images, said means being electrically connected to the planning console for receiving video signals therefrom relating to the images to be displayed, and/or to the image recording means.

According to another feature of the invention, the positioning robot arm has at least six degrees of freedom i.e. three translations and three rotations thanks to which the tool or the instrument and the like that it carries can be positioned and oriented in space in all possible ways.

According to another feature of the invention, the robot arm comprises a force sensor and is designed to operate according to a mode in which a user can move the robot arm manually by seizing it by its terminal portion. The robot arm then operates in a cooperative mode.

According to another feature of the invention, the planning console is equipped with a control screen and with a communication interface designed to receive operating planning parameters from a user.

Thanks to these arrangements, the processing means can take into consideration the operating planning parameters in order to control the trajectory of the positioning robot and in particular the trajectory of the tool or of the instrument, or of the image recording means that it carries.

Thus, the cranial entry point and the target point in the cervical mass, for example, can be furnished to the platform thanks to a simple and friendly graphical interface.

The communication interface can, for example, be in the form of a keyboard, of a tactile interface and/or of a pointing device, such as a mouse for example.

According to particular features of the invention, the processing means are designed to define each trajectory thanks to three-dimensional analyses made based on the operating planning parameters and on the spatial coordinates of the resetting elements.

According to another feature of the invention, the tools comprise at least one contact or contactless probe and/or at least one ultrasonic probe, and/or at least one rangefinder.

According to another feature of the invention, the probe is a mechanical pointing instrument designed to be removably fixed on the robot arm. In cooperative mode, the user can point an element on the patient's head by moving manually the pointing instrument and getting into contact with the target. Such a probe permits the user to acquire for example the positions of relevant anatomical points or the positions of radio-opaque markers or the positions of a multitude of points in contact with the patient's skin in order to obtain a surface therefrom by reconstruction.

According to another feature, the probe is a distance measuring optical module, for example a laser rangefinder.

Based on the data from coders of the robot arm, on the geometry of the probe and on the distance measurement provided by the optical module, the system can calculate the three-dimensional position of the point of the object intersected by the laser beam directly in the system of coordinates of the robot arm.

In this case, the probe provides a virtual contactless pointing solution. Analogously to the mechanical pointing instrument, such a probe permits the user to acquire the positions of relevant anatomical points, of radio-opaque markers or of a multitude of points in contact with the patient's skin in order to obtain a surface therefrom by reconstruction.

According to another feature of the invention, at least one of the tools is comprised of a tubular guide or guiding sleeve.

Thanks to these features, the robotized platform equipped with a tubular guide or with a sleeve mounted fastened on the receiving element of the positioning arm, can be used as stereotaxic frame, the sleeve maintained in a fixed spatial position by the positioning robot arm offering an axial guiding for a drill bit, for an electrode, for a needle and other instruments and means usable in the frame of stereotaxic neurosurgery.

When the pre-operating images (scanner, MRI or other method) and the position of the patient are put in correspondence, the system knows the position of the instrument(s) carried by the robot arm.

Said instrument positioned by the robot arm in correspondence with the planning can be a laser pointer or other pointer type. The laser pointer then permits to target on the patient an anatomical structure identified on the pre-operating imaging. In cooperative mode (as defined above), the user is capable of pointing a target on the patient's head by seizing, by its terminal portion, the robotized positioning arm equipped with a laser pointer, and moving it manually. The pointed direction is represented on the pre-operating images of the planning console.

The platform, object of this invention, then advantageously substitutes a neuro-navigation system.

The advantage of such a robot arm is that it can maintain the pointer in position, which is not the case with current neuro-navigation systems when the pointer is held manually.

According to another feature of the invention, at least one of the tools is comprised of a surgical instrument. In this way, the surgical action will be performed not by the surgeon but by the robot arm in correspondence with the planning.

The image recording means is designed to be removably fixed at the end of the robot arm. Said image recording means comprises at least one video camera of the digital type, for example.

Thanks to said image recording means, the user can visualize on the patient a region of interest, for example a region identified on the pre-operating imaging. In cooperative mode, as defined above, the user is capable of visualizing a region of his choice on the patient's head by seizing the positioning arm by its terminal portion and by moving it manually. The visualized region is represented on the pre-operating images of the planning console.

The means for displaying images obtained from the camera can for example, non-restrictively, be a screen of the type 2D and/or a helmet of the type 2D or even preferably of the type 3D if stereovision techniques are used. The platform, object of this invention, then substitutes advantageously a navigated surgical microscope. The video stream delivered by the image recording means can be transmitted simultaneously to the screen of the planning console. Thus, the surgeon and the rest of his team visualize the same video image of the anatomical region during operation. They can be transmitted to another visualization means but also, simultaneously, to that other visualization means and to the screen of the planning console.

Instead of manually moving the image recording means by seizing the robot arm in cooperative mode, the user can also guide the movements of the robot arm by means of a control box. The same control box permits the regulation of the camera(s) of the image recording means, in particular the zoom level and the focusing distance. This control box can comprise control buttons and/or at least one control lever.

Alternately, the positioning of the image recording means in cooperative mode, i.e. by seizing by its terminal portion the positioning arm equipped with said recording means and by moving it manually, can be made without spatial correspondence at the level of the planning console. The platform, object of this invention, is then the equivalent to a simple surgical microscope.

According to another feature of the invention, the means for recording images of the field of operation and other relevant anatomical regions, comprises a pair of stereoscopic cameras for example of the digital type in order to acquire two stereoscopic video images of the anatomical region to be processed and be able to render a 3D view of the region thanks to a stereoscopic images visualization system being part of the invention. The advantage of this method is to render the perception of the relief to the surgeon, thus improving the quality of his surgical action.

According to another feature of the invention, the image recording means includes an optical module designed to be interfaced to an optical cable connected itself to a cold light source. Thus, the device lights the anatomical region to be processed acquiring at the same time a video stream therefrom.

A well-known disadvantage of certain operating microscopes is that they require a powerful lighting of the anatomical region so that the image transmitted in the binoculars has a sufficient luminosity. The use of video cameras of the digital type is a positive advantage since they do not require a powerful lighting. An ambient lighting can then suffice for a correct vision of the anatomical region.

According to another feature of the invention, the image recording means includes two laser modules projecting visible laser beams. Said laser beams converge on one point which can be adjusted to be the point of intersection of the two optical axes of the stereoscopic cameras.

These convergent laser modules bring an advantage during the use, since they indicate the optimal working area for the perception of the relief. They are also advantageous in production for facilitating the centering of the two stereoscopic cameras on the same point and determining the geometry of the image recording means tool.

According to another feature of the invention, the image recording means includes a central laser module aligned with the central optical axis of the pair of stereoscopic cameras. Said visible laser beam materializes the axis in which the video image of the anatomical region is acquired.

According to another feature of the invention, the central laser module is a rangefinder laser capable of measuring the distance between its external face and the nearest object pointed by the laser beam.

According to another feature of the invention, the image recording means includes a mechanical system for rotation around its optical axis. The user can thus rotate the image recording means with the help of a handle in order to orient the video image of the anatomical region according to the needs of its surgical action.

According to another feature, the invention integrates a mechanical pointer equipped with at least one visible marker, itself well-known, designed to be located on the video images acquired by the image recording means. The position of the tip of the pointer can then be calculated by triangulation by identifying the marker(s) on the two stereoscopic images. This calculation requires first a calibration of each of the two cameras (intrinsic parameters) as well as calibration of the stereoscopic system (position and orientation of one camera with respect to the other). The advantage of this solution is that the pair of stereoscopic cameras is situated in an area near the anatomical region to be processed and that one thus gets rid of the <<line of sight>> problem common to existing optical localization neuronavigation systems.

When the pre-operating images (scanner, MRI or other method) and the position of the patient are put in correspondence, the system knows the position of the image recording means carried by the robot arm. The system can then advantageously substitute a microscope combined with a neuronavigation system. The point of interest displayed on the anatomical region and on the pre-operating images of the planning console can be for example the point of intersection of convergent laser beams and/or the point of impact of the central laser beam and/or the point in contact with the mechanical pointer equipped with visible markers.

According to another feature of the invention, a stereoscopic images visualization system of the three-dimensional type is provided.

According to a feature of the invention, the stereoscopic images visualization system is comprised of two screens designed to display two video images derived from different sources. Said screens can advantageously be mounted on a helmet or on glasses so that the surgeon keeps his hands free for his surgical action.

Said visualization system can be used during the intervention planning stage on the console for displaying a realistic view of the 3D virtual objects; for example, the digital model of the patient established based on the pre-operating images, or on the planning virtual objects such as a target point, an entry point, a rectilinear trajectory, a surface of interest, a volume of interest, etc.

The surgeon thus handles directly data in three-dimensional form, unlike the existing neuro-navigation systems, which only have a screen displaying data in two-dimensional form.

The device can also advantageously substitute an operating microscope by displaying through the visualization system the video images derived from the image recording means. The surgeon can then operate in the position he considers optimal for his surgical action.

Once the pre-operating images (scanner, MRI or other method) and the position of the patient in the operating theater are put in correspondence, the planning console knows the position of the image recording means carried by the robot arm. Knowing a priori the projective model of the cameras, it is possible to superimpose the virtual images on the real images in order to display a defined element of the targeted anatomical region. This element can be for example a tumor in case of a tumor resection, or a target point, or an entry point, or a trajectory, or an instrument, or even an anatomical region of interest. The stereoscopic visualization system then displays video images of the anatomical region, augmented with planning virtual elements. Then the function of augmented reality is ensured.

Augmented reality permits to provide precious data to the surgeon while he is operating. This is a very advantageous function because it permits the surgeon to avoid the situation in which he had to look alternately the region he was operating and the pre-operating images displayed on a screen and make the correspondence between said data mentally. All data are projected in a superimposed manner on the same screen. The stereoscopic visualization system can display in particular data in textual form, for example distances or volumes.

These features give the platform a multi-application nature corresponding to the needs of hospital centers in terms of logistical management and maintenance and meet the objectives of flexibility and versatility of the operating theater.

Another object of this invention is a method aiming at augmenting the precision of the resetting between the anatomical region to be processed, its digital model and a robotized arm.

To this end, the method according to the invention consists in:

acquiring, prior to the neurosurgical intervention, first digital images of the region to be processed and transferring said digital images to the planning console by means of a network or of a physical medium so that they are recorded and processed therein, acquiring in the per-operating stage, with the help of a scanning instrument carried by the element receiving the terminal distal segment of the robotized arm, second digital images of a pertinent portion of a body area of the patient appearing already on the first digital images, and transferring said second digital images to the planning console so that they are recorded and processed therein, building a first three-dimensional digital model based on the first digital images, said model showing the patient's pertinent body area, building a second three-dimensional digital model based on the second digital images, still showing the patient's pertinent body area, and putting in correspondence the first and second models by superimposition of the representations of the pertinent body area appearing on one model and on the other.

Thus, such a method does not require the presence of radio-opaque markers and increases the degree of precision of the resetting between the pre-operating model, the patient and the robotized arm.

BRIEF DESCRIPTION OF THE FIGURES AND OF THE DRAWINGS

Other advantages and features of the invention will appear while reading the description of a preferred embodiment given as a non-restrictive example referring to the attached drawings, in which.

Figure 1:
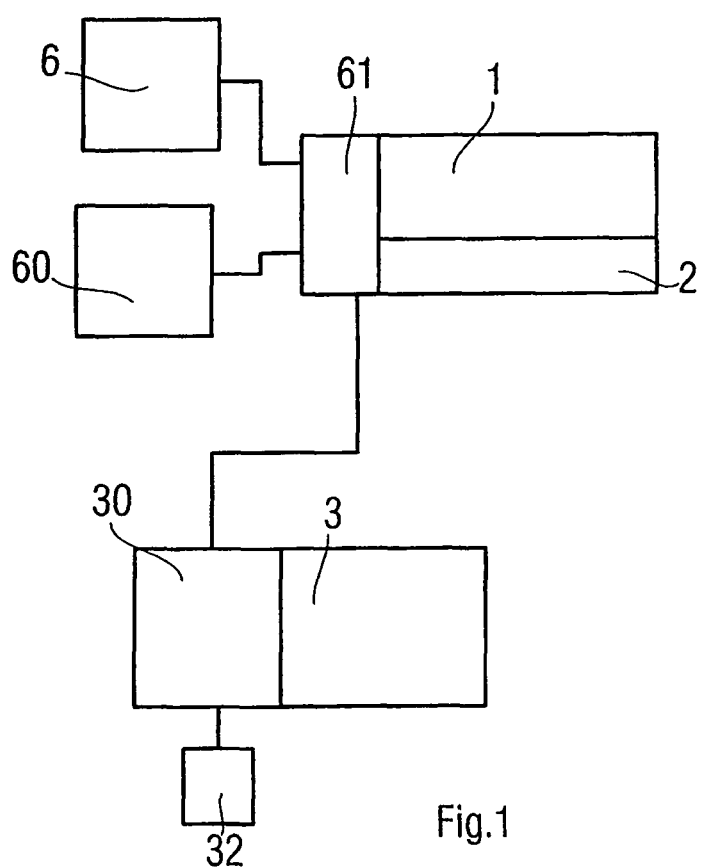
FIG. 1 is a synoptic view of the platform according to the invention.
Figure 2:
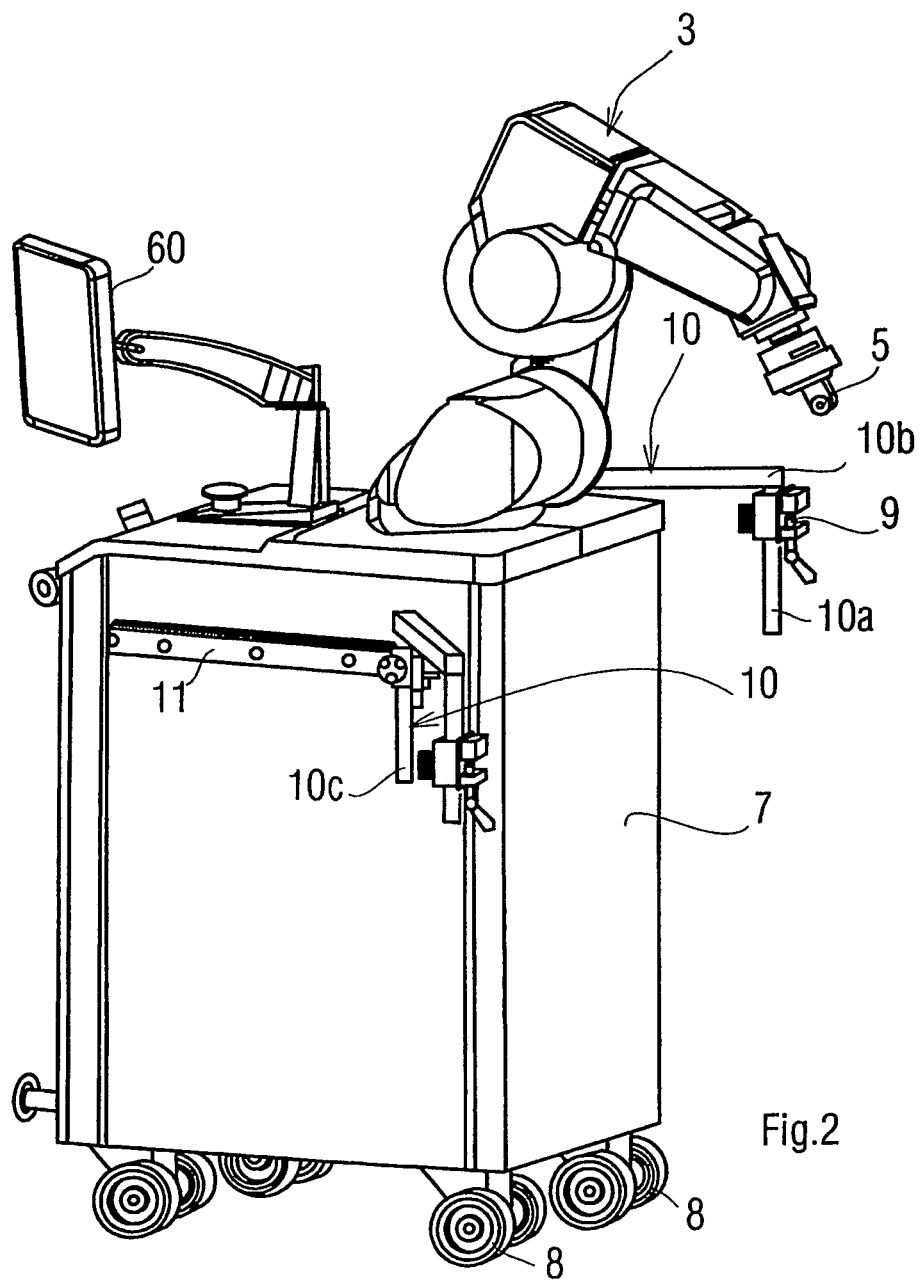
FIG. 2 is a perspective view of a platform according to the invention.
Figure 3:
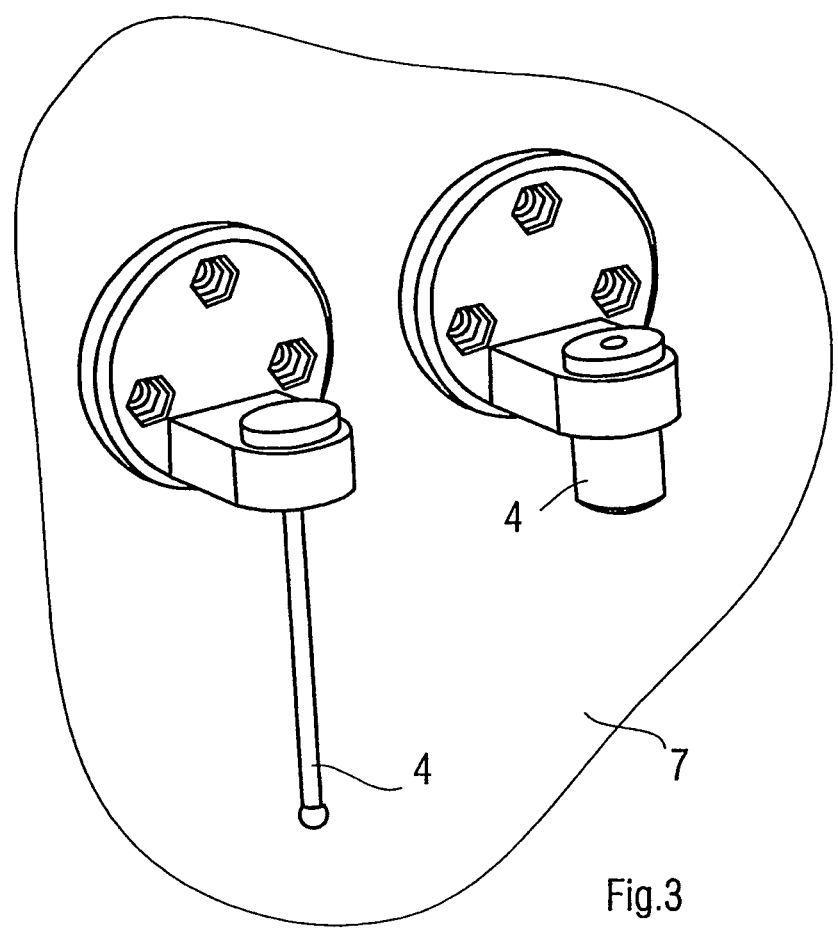
FIG. 3 is a detailed view of the platform according to the invention.
Figure 4:
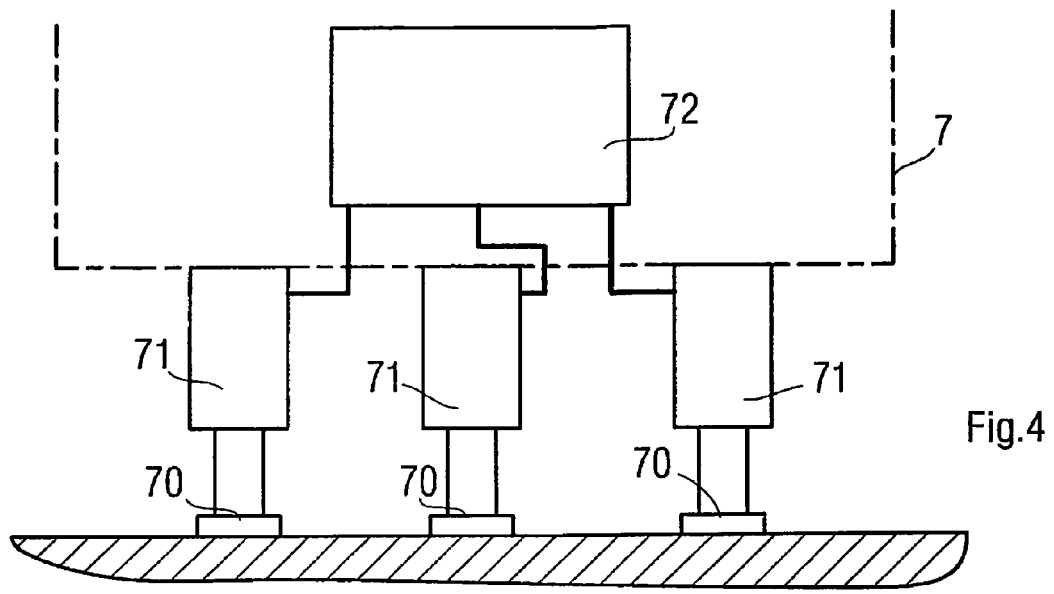
Figure 5:
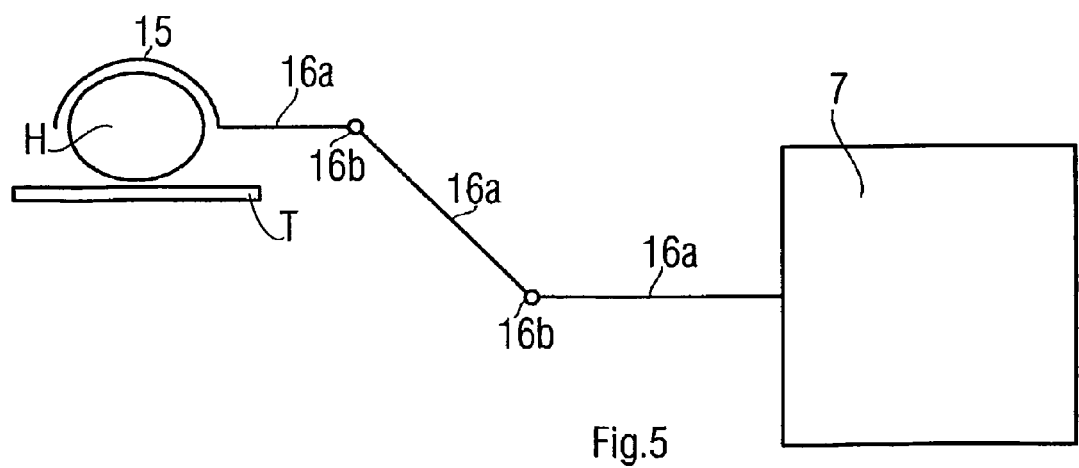
Figure 7:
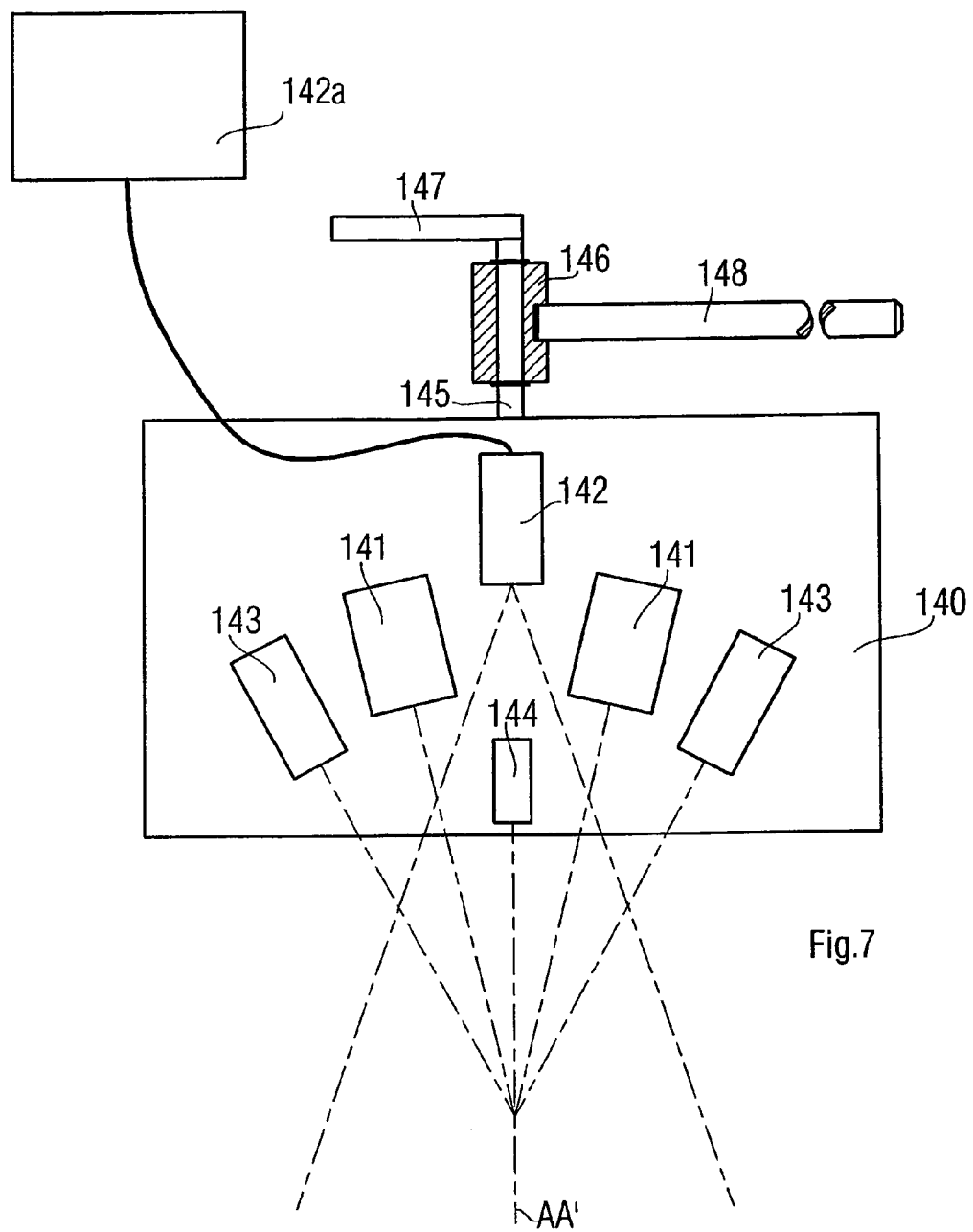
Figure 6:
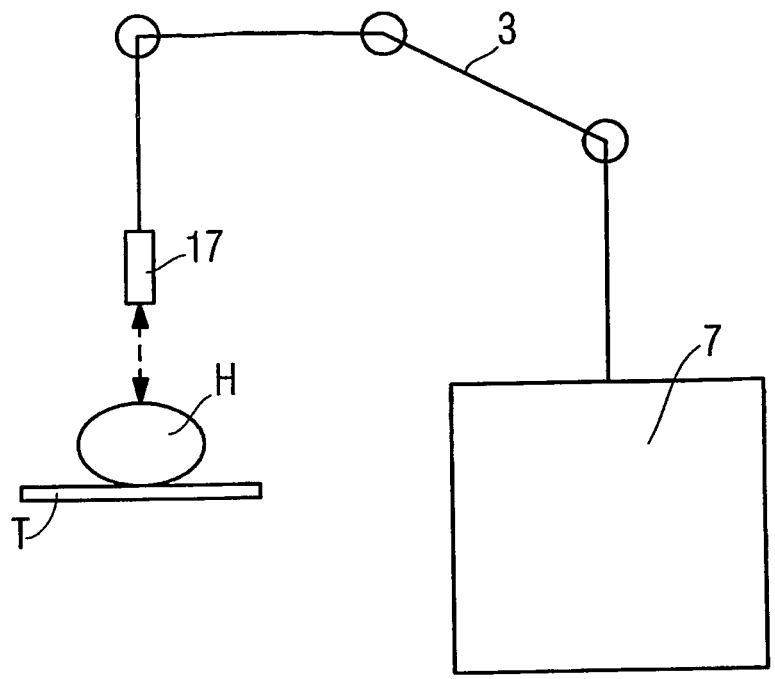
Figure 8:
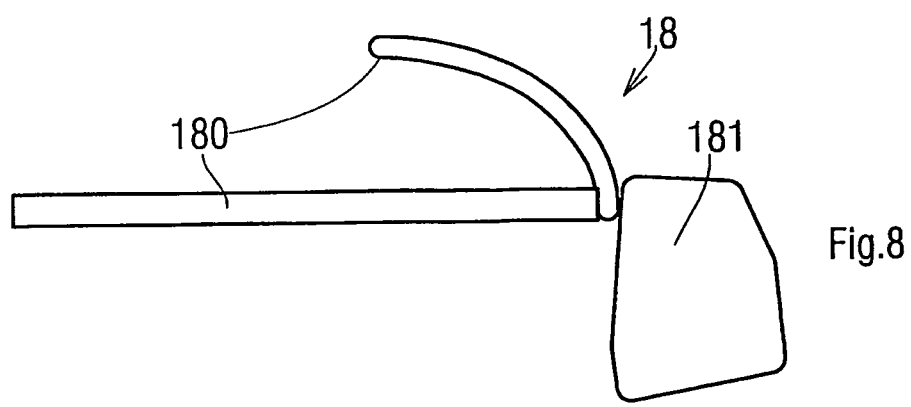
Figure 9:
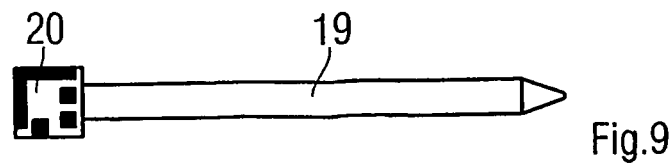

FIG. 4 is a schematic view showing an exemplary embodiment of means for immobilizing the box with respect to the floor, said means being in an unfolded position, FIG. 5 is a schematic view of an exemplary embodiment of means for fixing the box to a head rest designed for receiving the head of the patient to be operated, FIG. 6 is a schematic view of an exemplary embodiment of a contactless probe carried by the robot arm, FIG. 7 is a schematic view of an exemplary embodiment of an image recording means, FIG. 8 is a schematic view of an exemplary embodiment of visualization means of the three-dimensional type, FIG. 9 is a schematic view of an exemplary embodiment of a mechanical pointer equipped with a visible marker.

IMPROVED MANNER FOR IMPLEMENTING THE INVENTION

As shown, the multi-application robotized platform for neurosurgery, according to the invention, includes a planning console 1, which can be loaded, comprising processing means 2 capable, in particular, of receiving and processing digital images, a robotized positioning arm 3 comprising a plurality of arm segments, one of which is terminal and proximal and the other is terminal and distal, said segments being interconnected by articulated elements and the terminal distal arm segment comprising a receiving element 5 arranged in such a way as to receive, in a fixed state, removably, tools 4, instruments, and the like, said robot arm being guided by the planning console 1.

The platform also comprises a set of tools and possibly surgical instruments designed to be positioned and removably fixed to the receiving element 5 of the terminal distal arm segment as explained previously, as well as a means 14 for recording video images of the field of operation and means for displaying 6 pre-operating and per-operating images. Said visualization means are electrically connected to the planning console for receiving video signals therefrom related to the images to be displayed, and/or to a means 14 for recording video images such as a camera.

The visualization means can include visualization means of the three-dimensional type.

The platform will also be equipped with a control screen 60 and with a communication interface 61 designed to receive operating planning parameters from a user.

A central unit and a data input computer interface, which can be part of the abovementioned communication interface, are associated to the positioning robot arm 3.

The robotized positioning arm 3, by its terminal proximal segment, is fixed to an orientation turret installed fixedly on the upper portion of a parallelepipedal box 7. This box contains electronics suitable in particular for controlling the arm 3.

Between the arm segments of the positioning robot arm 3 are provided articulated elements, for example six, comprising motors and incremental coders associated, at the level of each articulated element, to the axle or to each of the swivel pins defined by the latter. Each motor is capable of driving into rotation two contiguous segments one with respect to the other and each associated incremental coder is capable of providing information relative to the angular position of one of these segments with respect to the other. The articulated elements permit to position the terminal tool, the instrument and the like, both in position (three degrees of freedom) and in orientation (three degrees of freedom). The angular values measured by the incremental coders permit, thanks to the known geometry of the robotized arm and to the known geometry of the tool, instrument and the like carried by the arm 3, to calculate the Cartesian position of the distal end of the robotized arm, the Cartesian position of the end of the tool, instrument and the like and the orientation of the latter in space.

The arm, as described, receives an appropriate fairing so as to have a minimum of nooks in order to avoid the risk of dust or pathogenic elements penetrating and thriving therein.

The box 7 comprises in its lower portion omnidirectional rolling elements 8 such as casters carried each by an omnidirectional mounting having a vertical rotation axis. Said casters 8 and mountings ensure an easy movement on the ground.

The box 7 comprises means for immobilization with respect to the floor so as to prevent its movement during the surgical intervention.

According to a first embodiment, these immobilization means are comprised of blocking elements, well-known per se, associated to the casters 8 and to the mountings, when they are activated, prevent the rotation of the casters around their natural axis of rotation and the pivoting of the mounting around the vertical axis. The box is thus immobilized with respect to the floor.

According to a variant embodiment, as shown in FIG. 4, the means for immobilizing the box 7 with respect to the floor are comprised of at least three feet 70 that can occupy either a retracted position according to which they are placed away from the floor, or an unfolded position according to which they are placed in contact with the floor in order to immobilize the box, each foot 70 being moved from one position to the other by a driving mechanism 71.

According to a particular embodiment, each foot is formed by the terminal portion of the rod of a hydraulic single-action jack associated to an appropriate hydraulic circuit 72 common to different jacks, comprising in particular, as well known, at least one hydraulic distributor and a hydraulic pump driven by an electric motor guided by a remote control. The distributor or each distributor will be electrically controlled, for example. The motor 71 can also be formed of an electric jack.

Thus, the user can let the feet 70 down in order to stabilize the box 7, without exerting any particular effort.

The box 7 can be provided with means for fixing to a surgical table on which the patient to be operated has been placed beforehand, the head H of the latter being maintained firmly in an appropriate position by a head rest that is fixed with respect to the table.

The means for fixing the box 7 to the operating table prevent any movement of the box with respect to said table and are comprised of two mounting flanges 9 capable of cooperating, each, in a fixed state with one of the rails of the table, each flange being brought adjustably in position by a support structure 10 integral with a support rail 11 carried by one of the sides of the box 7. The shape and dimensions of each mounting flange 9 are compatible with those of the rails of the table. Each support structure 10 is formed of a vertical arm 10a receiving the corresponding mounting flange 9. This flange 9 is mounted with a possibility for movement in height along the vertical arm 10a and comprises a tightening element such as a compression screw or the like, for immobilization on the arm 10a according to the appropriate position. Each support structure also has a horizontal arm 10b fixed to the vertical arm 10a. This horizontal arm 10b comprises a second vertical arm 10c introduced in a slide mounted adjustably in position in the support rail 11 of the box 7. This second vertical arm will be immobilized in the slide by means of a screw, which also ensures the immobilization of the slide in the support rail 11.

According to another embodiment, as shown in FIG. 5, the box 7 is no longer fixed to the operating table T, but directly to a head rest 15 designed for receiving the head H of the patient to be operated, the latter being placed on the operating table T. This box 7 is connected to the head rest 15 through specific fixing means ensuring, when it is activated, a rigid link between the box 7 and the head rest 15. This arrangement has the advantage of being rid of the flexibility of the operating table T. These fixing means can be placed in a so-called inactive state permitting the appropriate positioning of the box 7 with respect to the head rest 15.

As a non-restrictive example, this means can be formed of an articulated mechanical arm 16, comprised of several arm segments 16a connected two by two by articulated elements 16b associated to immobilization flanges, not shown, that can each occupy either a locked position of the associated articulated element or an unlocked position of the latter.

As mentioned above, a central unit 30 and a data input computer interface 32 are associated to the positioning robot arm 3.

The central data unit 30 can be placed in the box and be part of the electronics the latter transports.

The robotized platform can also include a contact or contactless probe.

The contact probe can be formed of a mechanical pointer carried by the terminal distal segment of the robot arm. Said mechanical pointer designed to be brought into contact with the target to be acquired can include a pointing ball or a dry point.

A contactless probe 17 formed of a distance measuring optical module such as, for example, a laser rangefinder, is schematically shown in FIG. 6 in association with a robot arm 3. One can see in this Figure that said probe 15 is carried by the terminal distal segment of the robot arm and is oriented toward a characteristic point of the head H of the patient.

The image recording means 14 comprises at least one video camera of the digital type, for example. In a preferred embodiment, as shown in FIG. 7, the means for recording images of the field of operation comprises, on a support plate 140, two stereoscopic cameras 141, for example of the digital type, in order to acquire two stereoscopic video images of the anatomical region to be processed and so as to be able to render a 3D view of said region thanks to a stereoscopic image visualization system as described below. It should be noted that said two cameras 141 are arranged symmetrically with respect to the central optical axis AA'.

Said image recording means is in addition provided with an optical module 142 designed to be interfaced to an optical cable 143 itself connected to a cold light source 142a in order to light the anatomical region to be processed.

According to an advantageous arrangement of the invention, the image recording means 14 comprises two laser modules 143 lateral with respect to the cameras 141 and preferably arranged symmetrically with respect to the optical axis AA'. Said laser modules 143 project visible laser beams and are oriented so that their beams converge on a point that can be adjusted to be the point of intersection of the two optical axes of the stereoscopic cameras. As shown, the point of convergence belongs to the optical axis AA'.

These convergent laser modules 143 offer an advantage during the use, since they indicate the optimal working area for the perception of the relief. They are also advantageous in production for facilitating the centering of the two stereoscopic cameras on the same point and determining the geometry of the image recording means tool.

The image recording means 14 comprises, in addition, a central laser module 144 aligned with the central optical axis AA'. This visible laser beam materializes the axis in which the video image of the anatomical region is acquired.

The laser module 144 is a rangefinder laser capable of measuring the distance between its external face and the nearest object pointed by the laser beam.

The image recording means 14 can include a mechanical system for rotation about its optical axis AA' permitting the orientation of the video image formed on the visualization means.

Such a rotation system can be made by means of a pivot link or pivot sliding with the whole of the elements described above, integral with a shaft 145 introduced with adjustment sliding in the through bore of a sheath 147 provided with a support 148 for removable fastening to the receiving element 5 of the terminal distal segment of the robotized arm. This shaft 145 can be fixed rigidly to the plate 140.

Externally to the sheath 146, the shaft 145 will receive a handle for pivotal operating 147 through an action on which the image recording means 14 can be oriented appropriately. A tightening mechanism with jaws for example, not shown, can be attached to the sheath 146, designed to exert a tightening effort on the shaft 145 when it is activated in order to prevent any pivoting movement of the recording means 14 with respect to the sheath 146. This jaw mechanism can be made inactive by acting on a control installed on the handle 147. When inactive, said tightening mechanism permits the pivoting of the recording means 14 with respect to the sheath 146.

FIG. 8 represents an exemplary embodiment of visualization means 18 of the three-dimensional type. This stereoscopic visualization means, designed to be carried by the surgeon, includes a helmet 180 designed to be inserted onto the head of the surgeon and two visualization screens 181 that can be positioned in front of the eyes of the surgeon. The visualization screens can display video images of the anatomical region to be processed, possibly enriched with virtual elements of the planning in order to ensure an augmented reality functioning.

FIG. 9 represents a mechanical pointer 19 equipped with at least one visible marker 20, designed to be located on the video images acquired by the image recording means. It can be seen in this Figure that the marker 20 comprises strongly contrasting areas in this particular case white areas and black areas. Thanks to the marker 20 the spatial position of the tip of the pointer 19 can be calculated by triangulation by identifying the marker on the two stereoscopic images provided by the two video cameras of the image recording means 14.

The robotized platform object of this invention permits the positioning of a guide, of a probe or of a video image recording means. Its utilization is based on four stages:

a first stage of acquiring digital images (scanner or MRI) of the region to be processed and transferring these digital images to the planning console 1 by means of a network or of a physical medium, a second stage of processing said images, identifying the anatomical structures and planning the surgical action, for example the definition of an entry point and of a target point for establishing a trajectory of a biopsy needle, a third stage of putting in correspondence the pre-operating images with the position of the patient's head in per-operating phase according to one of the embodiments described below, and finally a last stage of automatic positioning of a terminal tool 4, for example a guide, a laser pointer, a camera, a capturing device and the like.

The robotized platform according to the invention takes up the same hypotheses regarding the sagging of the brain and the possible flexion of the needles, as well as the stereotaxic frames, the neuro-navigation systems and the robotic systems.

The pre-operating images can be put in correspondence with the position of the patient in the operating theater in several ways thanks to the different technologies integrated in the platform.

According to a first embodiment, the resetting method resorts to radio-opaque markers.

During the intervention, the pre-operating images (scanner or MRI or other method) can be put in correspondence with the position of patient's head thanks to markers designed to be located on the imaging, for example radio-opaque markers. In this case, said markers are placed on patient's head prior to the acquisition of the pre-operating images. They are identified on the images during planning stage in order to determine their position in the image mark (automatically with a possibility of a manual retouching).

During the intervention, the surgeon places the robotized positioning arm in cooperative mode and manually moves said positioning robot arm equipped with a probe in order to locate the positions of the different markers in the robot mark. Once the positions of markers in the image mark and in the robot mark are known, a point-by-point resetting algorithm permits to put the two marks in correspondence.

This method can be implemented with different types of probe: the mechanical pointing instrument and the virtual contactless probe (laser rangefinder).

Alternately, the surgeon places the robot arm equipped with the image recording means 14 above the head of the patient. The surgeon can then manually proceed to the detection of the radio-opaque markers by using the mechanical pointer 19 equipped with black and white visible markers 20. The system can also proceed automatically to the detection of the radio-opaque markers by positioning the image recording means 14 in different positions around the head H of the patient, acquiring stereoscopic images containing radio-opaque markers, segmenting the images for locating the radio-opaque markers and calculating by triangulation of their three-dimensional positions in the system of coordinates of the robot arm. In order to facilitate the detection of the radio-opaque markers, specific markers having a strong contrast in the visible spectrum can be used.

Once the positions of the markers in the image mark and in the robot mark are known, a point-by-point resetting algorithm permits to put the two marks in correspondence.

According to another embodiment, the method does not resort to radio-opaque markers.

Alternatively, the putting in correspondence of the image and robot marks is made based on anatomical surface marks instead of markers. During the intervention, the surgeon manually moves the positioning robot arm equipped with a probe in order to locate the positions of characteristic anatomical points or surfaces such as the nose, arches, ears, teeth or other. A dots-surface or surface-surface resetting algorithm permits to reset the dots or surfaces thus acquired with the pre-operating examinations.

This method can be implemented with different types of probe: the mechanical pointing instrument, the virtual contactless probe (laser rangefinder), the mechanical pointer equipped with black and white visible markers.

This method for putting in correspondence has the advantage of not requiring any installation of markers on patient's head prior to the imaging.

According to the method explained above, the robot arm is manually moved by the surgeon.

Alternatively, the acquisition of characteristic anatomical surfaces is made contactless and automatically, by scanning the whole or portion of the head H of the patient. Such an acquisition can be obtained by a contactless measuring sensor 4 for example a laser rangefinder, fixed at the end of the positioning robot arm 3. Said robot arm automatically scans the region of interest by driving said sensor 4 according to an appropriate movement in front of said region of interest, for example, at constant speed according to a rectilinear translation movement. Knowing the exact position of the sensor 4 in the robot mark permits the reconstruction of anatomical surfaces.

This method can also be implemented with the image recording means when it comprises a laser rangefinder. This is particularly advantageous during a navigated microscopy procedure, because it is no longer necessary to change the tool during the intervention.

An echographic probe can also be used instead of the contactless measuring sensor. In this case, the putting in correspondence of the image and robot marks can be made thanks to a processing algorithm based on the properties of the image such as intensity, gradient, and other properties.

These automatic methods for putting in correspondence do not require any manual intervention by the surgeon.

Once the putting in correspondence is done, the robot automatically positions the tool attached to the receiving element on the planned trajectory.

It stands to reason that this invention can receive all variants within the field of technical equivalents without however departing from the scope of this patent as defined by the claims below.

The invention claimed is:

1. Multi-application robotized platform for neurosurgery, wherein the platform comprises:
a planning console comprising processing means capable of receiving and processing digital images,
a positioning robot arm comprising a plurality of arm segments, one of which is terminal and proximal and the other is terminal and distal, said segments being interconnected by articulated elements and the terminal distal arm segment comprising a receiving element arranged in such away as to receive tools, said robot arm being guided by the planning console, at least one means for recording video images capable of recording images of an anatomical region to be processed, said means being electrically connectable to the processing means that the planning console includes, and said recording means being capable of being positioned and removably fixed to the receiving element of the distal arm segment, said means for recording video images comprising a central optical axis (AA') and integrating a central laser module aligned with the central optical axis (AA'), said central laser module being a rangefinder laser capable of measuring the distance between its external face and the nearest object pointed by the laser beam, tools and/or instruments, and the like, designed to be positioned and removably fixed to the receiving element of the terminal distal arm segment, visualization means for displaying pre-operating and per-operating images, said means being electrically connected to the planning console for receiving video signals therefrom relating to the images to be displayed, and/or to the image recording means wherein the means for recording video images of the anatomical region to be processed includes two stereoscopic cameras in order to acquire two stereoscopic video images of the anatomical region to be processed and that the visualization means comprise a stereoscopic images visualization system, the image recording means further comprises two laser modules projecting visible laser beams convergent on a point capable of being adjusted so as to be the point of intersection of the two optical axes of the stereoscopic cameras.

2. Platform according to claim 1, wherein a central unit and a data input computer interface are associated to the positioning robot.

3. Platform according to claim 1, wherein the platform is equipped with a control screen and with a communication interface designed to receive operating planning parameters from a user.

4. Platform according to claim 2, wherein the processing means are designed to define a trajectory by three-dimensional calculations made based on the operating planning parameters and on spatial coordinates of anatomical marks.

5. Platform according to claim 1, wherein the tools comprise at least one guide, and/or at least one mechanical pointer, and/or at least one laser pointer, and/or at least one ultrasonic probe, and/or at least one rangefinder and/or at least one surgical instrument.

6. Platform according to claim 1, wherein the image recording means comprises a mechanical system for rotation around its optical axis.

7. Platform according to claim 1, wherein the visualization means displays video images of the anatomical region to be processed augmented with virtual elements in order to ensure an augmented reality functioning.

* * * * *